US012702296B2

(12) United States Patent
Guo

(10) Patent No.: US 12,702,296 B2
(45) Date of Patent: Aug. 11, 2026

(54) APERTURE-OPTIONAL HEAD-MOUNTED LOW-LIGHT FUNDUS IMAGING DEVICE

(71) Applicant: Welch Allyn, Inc., Skaneateles Falls, NY (US)

(72) Inventor: Lei Guo, Manlius, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 299 days.

(21) Appl. No.: 18/235,630

(22) Filed: Aug. 18, 2023

(65) Prior Publication Data

US 2024/0057863 A1 Feb. 22, 2024

Related U.S. Application Data

(60) Provisional application No. 63/399,630, filed on Aug. 19, 2022.

(51) Int. Cl.
*A61B 3/12* (2006.01)
*A61B 3/00* (2006.01)
(Continued)

(52) U.S. Cl.
CPC .............. *A61B 3/12* (2013.01); *A61B 3/0025* (2013.01); *A61B 3/14* (2013.01); *A61B 2090/502* (2016.02)

(58) Field of Classification Search
CPC ... A61B 3/0008; A61B 3/0025; A61B 3/0033; A61B 3/0041; A61B 3/005; A61B 3/0075; A61B 3/0091; A61B 3/022; A61B 3/024; A61B 3/028; A61B 3/063; A61B 3/10; A61B 3/102; A61B 5/117; A61B 5/6803; G02B 27/0172; G02B 27/0176; G08B 21/182
See application file for complete search history.

(56) References Cited

U.S. PATENT DOCUMENTS

| | | |
|---|---|---|
| 8,353,595 B2 | 1/2013 | Mann |
| 9,770,168 B2 | 9/2017 | Pohjanen et al. |

(Continued)

FOREIGN PATENT DOCUMENTS

| | | |
|---|---|---|
| CN | 112075920 | 12/2020 |
| CN | 112220448 | 1/2021 |

(Continued)

*Primary Examiner* — Nelson M Rosario
(74) *Attorney, Agent, or Firm* — Lee & Hayes, P.C.

(57) ABSTRACT

An aperture-optional head-mounted low-light fundus camera is provided. A fundus camera is configured to enclose a patient's eyes, orient imaging paths of image sensors and lenses towards the patient's eyes without requiring integral aperture stops within the enclosure, and provide non-pupillary low-light illumination for fundus imaging within the enclosure. The aperture-optional head-mounted low-light fundus camera can be worn by a patient during use without limiting the patient's movement or posture, alleviating awkwardness and discomfort caused to the patient by conventional fundus cameras. The aperture-optional head-mounted low-light fundus camera further improves image capture quality over conventional fundus cameras, by removing the need to use dexterity to align with eye pupil, minimizing image blur from errant movement, and eliminating visual artifacts from glares, haloes, reflections, and the like.

19 Claims, 6 Drawing Sheets

(51) Int. Cl.

| | |
|---|---|
| ***A61B 3/14*** | (2006.01) |
| *A61B 90/50* | (2016.01) |

(56) References Cited

U.S. PATENT DOCUMENTS

| | | | | |
|---|---|---|---|---|
| 10,888,222 | B2 * | 1/2021 | Monhart .................. | A61B 3/11 |
| 2007/0030448 | A1 | 2/2007 | Biernat et al. | |
| 2014/0267668 | A1 * | 9/2014 | Ignatovich ............. | A61B 3/125<br>348/78 |
| 2019/0008382 | A1 | 1/2019 | Toslak et al. | |
| 2021/0145276 | A1 | 5/2021 | Yao et al. | |
| 2021/0186319 | A1 | 6/2021 | Straub et al. | |
| 2025/0204772 | A1 * | 6/2025 | Jackson ................. | A61B 3/005 |

FOREIGN PATENT DOCUMENTS

| | | |
|---|---|---|
| EP | 3884843 | 9/2021 |
| WO | WO2020121243 | 6/2020 |

* cited by examiner

APERTURE-OPTIONAL HEAD-MOUNTED LOW-LIGHT FUNDUS IMAGING DEVICE

CROSS REFERENCE TO RELATED APPLICATION

This application is a Nonprovisional of, and claims priority to, U.S. Provisional Patent Application No. 63/399,630, filed Aug. 19, 2022, the entire disclosure of which is incorporated herein by reference.

BACKGROUND

In the field of ophthalmology, clinicians diagnose eye health and eye diseases of patients by operating fundus cameras to image the fundus—the rear interior of the eye. Fundus cameras are complex systems that combine optical, mechanical, and electronic components, designed according to standards such as ISO 10940:2009 and ANSI Z80.36-2021. Fundus cameras are used alongside ophthalmoscopes during eye examinations by clinicians, where ophthalmoscopes allow a clinician to examine the fundus directly, fundus cameras allow a clinician to capture images of the fundus for later review. Fundoscopy assists clinicians by capturing images that may be reviewed on demand, e.g., without the patient's presence.

Fundus cameras are typically large, expensive, and non-portable machines. Some common models include one or more components the size of a shoe box or larger, weighing several pounds, and costing anywhere from $3,000 to $20,000. Furthermore, fundus cameras operate by requiring a patient's head and eye to remain still in an unnatural position and require a bright, discomforting trans-pupillary light to illuminate the fundus for imaging. Although such illumination, in accordance with promulgated standards as mentioned above, is safe for patients, patients may still have unpleasant experiences during fundus imaging due to the pulsing of bright lights in close proximity to their eyes.

Additionally, training is typically required to overcome physical dexterity challenges in fundus photography, as the photographer must learn to manually align the camera with the very small opening provided by the pupil of the human eye, which is subject to constant, involuntary micro-movements that may blur captured images. Furthermore, successfully captured images can be suboptimal due to improper focus, errant movement, and uncontrollable eye micro-movements. Accordingly, fundus cameras incorporate increasingly complex optical and mechanical systems to improve image capture, further compounding their size, cost, and non-portability.

Moreover, due to the light path for trans-pupillary illumination and the imaging path of the camera sensor being limited to a substantially similar path by the narrowness of eye pupils, current fundus camera technology may still capture glares and haloes in fundus images resulting from stray light reflected back at the camera image sensor, and from cornea and crystalline lens reflections. Fundus cameras can incorporate polarizers in the imaging and illumination paths to mitigate, but not eliminate, such imaging artifacts.

Thus, there is a need for low-cost, portable fundus imaging device with better performance and improved usability.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Devices and systems discussed herein are directed to implementing cameras, and more specifically providing an aperture-optional head-mounted low-light fundus imaging device. A fundus imaging device is configured to enclose an area around a patient's eyes to orient imaging paths of image sensors and lenses towards the patient's eyes without necessarily requiring an integral aperture stop within the enclosure. The fundus imaging device may further provide non-pupillary low-light illumination for fundus imaging within the enclosure. Such an aperture-optional head-mounted low-light fundus imaging device may be worn by a patient during fundus photography without limiting the patient's movement or posture, alleviating awkwardness and discomfort caused to the patient by conventional fundus imaging devices. Such an aperture-optional head-mounted low-light fundus imaging device is also substantially reduced in mechanical, electronic, and optical components compared to conventional fundus imaging devices, reducing mass, weight, and cost. Such an aperture-optional head-mounted low-light fundus imaging device furthermore improves image capture quality over conventional fundus cameras by removing the need to use dexterity to align with eye pupil, minimizing image blur from errant movement, and eliminating visual artifacts from glares, haloes, reflections, and the like.

Figure 1A:
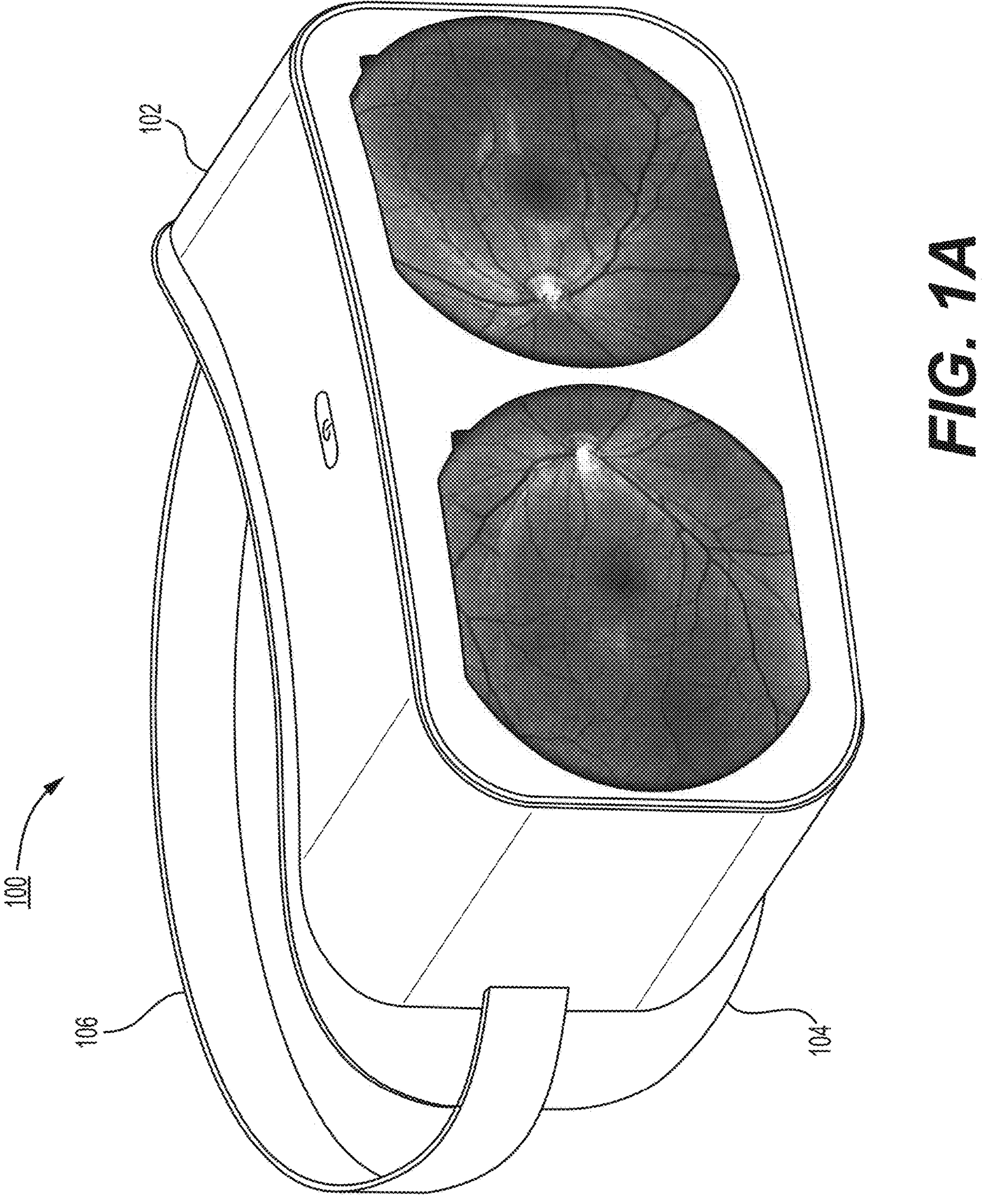
FIGS. 1A and 1B illustrate a fundus imaging device according to example embodiments of the present disclosure.
Figure 1B:
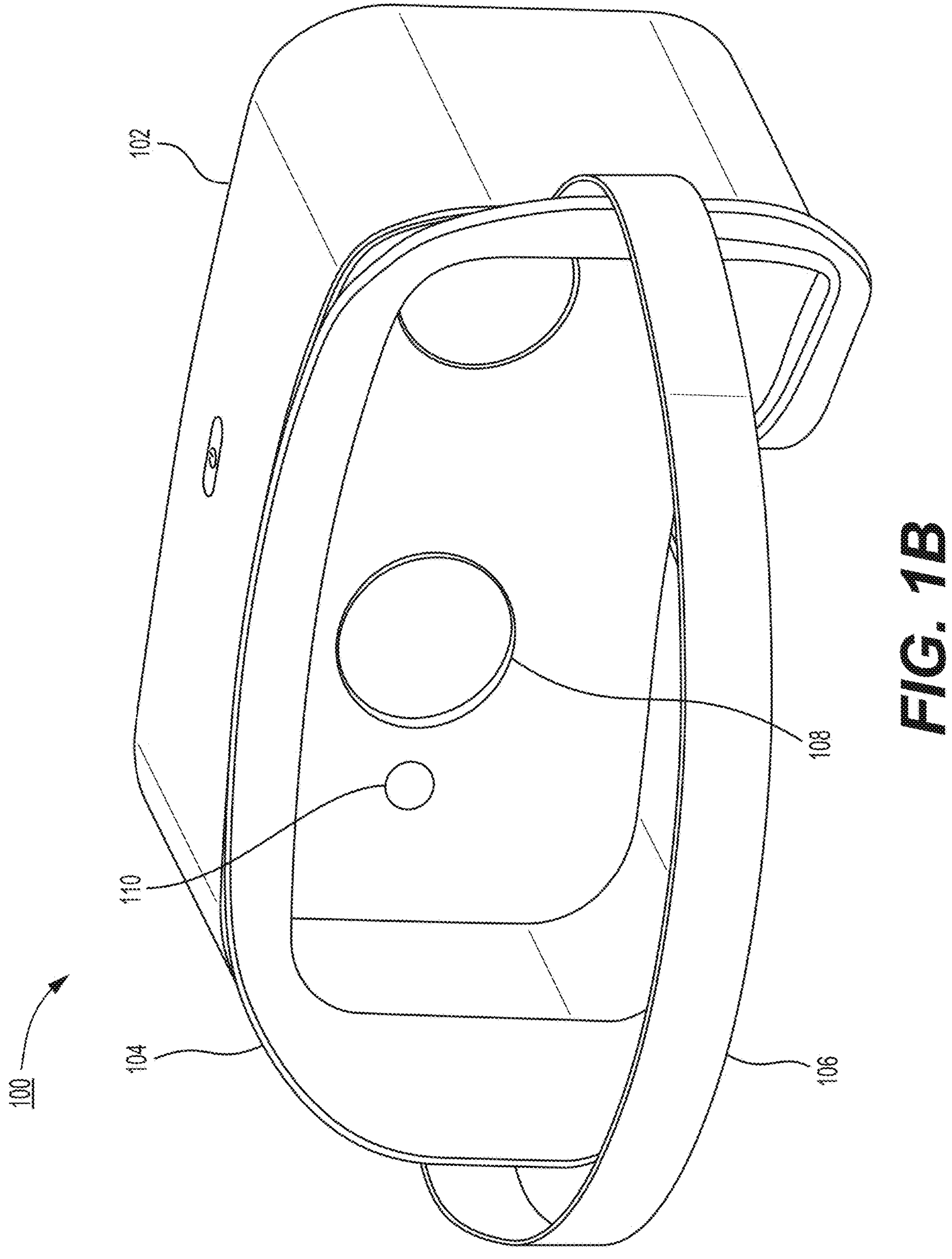

FIGS. 1A and 1B illustrate a fundus imaging device 100 according to example embodiments of the present disclosure. The fundus imaging device 100 includes a camera housing 102, an eye enclosure 104, and a head fastener 106.

The head fastener 106 may include any temples, arms, straps, strings, helmet, or any other member configured to fasten the camera housing 102 in front of the eyes on a head of a patient. The head fastener 106 may be adjustable in length, size, elasticity, friction, fit, and the like. The head fastener 106 may be replaceable with any other head fastener which varies in length, size, elasticity, friction, fit, and the like. Thus, the camera housing 102 has a side which is fastened in front of the eyes of a head of a patient, and this side shall be subsequently referred to as an "eye-facing side" of the camera housing 102. The camera housing 102 has an internal cavity (such as illustrated in FIG. 1B), which is open on the eye-facing side of the camera housing 102. The camera housing 102 can be closed on each side other than the eye-facing side.

The eye enclosure 104 lines an edge of the camera housing 102 on the eye-facing side of the camera housing 102. The eye enclosure 104 can be a lining member formed from an opaque, light-blocking material which is furthermore non-rigid so as to enclose a patient's eyes while fitting the contours of the patient's face surrounding the eyes without inducing discomfort. By way of example, the eye enclosure 104 may be formed from an elastomer, a foam, a fabric, a rubber, and the like.

Within internal cavity of the camera housing 102, one or more cameras (illustrated herein by the camera optics 108 of the one or more cameras visible in the view of FIG. 1B) are housed. Camera optics 108 of each camera within the camera housing 102 include at least an entry optic (which, as shall be illustrated by the subsequent examples (e.g., in FIGS. 2A-2C), may include an objective lens assembly, a prism, a lens, or otherwise any optic closest to eyes of a patient while the camera housing 102 is fastened to a head of the patient), and an image sensor behind the entry optic. A light-sensitive side of each image sensor is positioned in the internal cavity facing outward, toward the eye-facing side. The camera housing 102 is configured to be fastened to a head of a patient such that a light-sensitive side of each image sensor faces eyes of the patient, with camera optics including at least an entry optic between each image sensor and an eye of the patient. In this fashion, light exiting a pupil of the patient is incident upon one or more entry optics of the one or more cameras (subsequently referred to as "incident light," for brevity).

The camera housing 102 may further include in some examples, but need not include in all examples, an integral aperture stop which forms an intrinsic entrance pupil, where the entry optic is exposed to incident light within the eye enclosure 104 through the intrinsic entrance pupil. In the event that the camera housing 102 does not include an integral aperture stop which forms an intrinsic entrance pupil, a pupil of the patient serves as an extrinsic entrance pupil.

It should be understood that according to optical systems, an entrance pupil is a conceptual location at or behind an outer optical surface of a camera. The location and size of the entrance pupil correspond to a field of view of the camera, in turn. An entrance pupil should not be understood as being a tangible component of a camera.

In the event that the camera housing 102 includes an integral aperture stop which forms an intrinsic entrance pupil, contrary to traditional fundus cameras, a diameter of the intrinsic entrance pupil can be arbitrarily large relative to a dilated pupil of a patient. By way of example, eye pupils are generally approximately 4 mm in diameter, accordingly, a diameter of the intrinsic entrance pupil can therefore be arbitrarily larger than 4 mm.

Figures 1C, 1D:
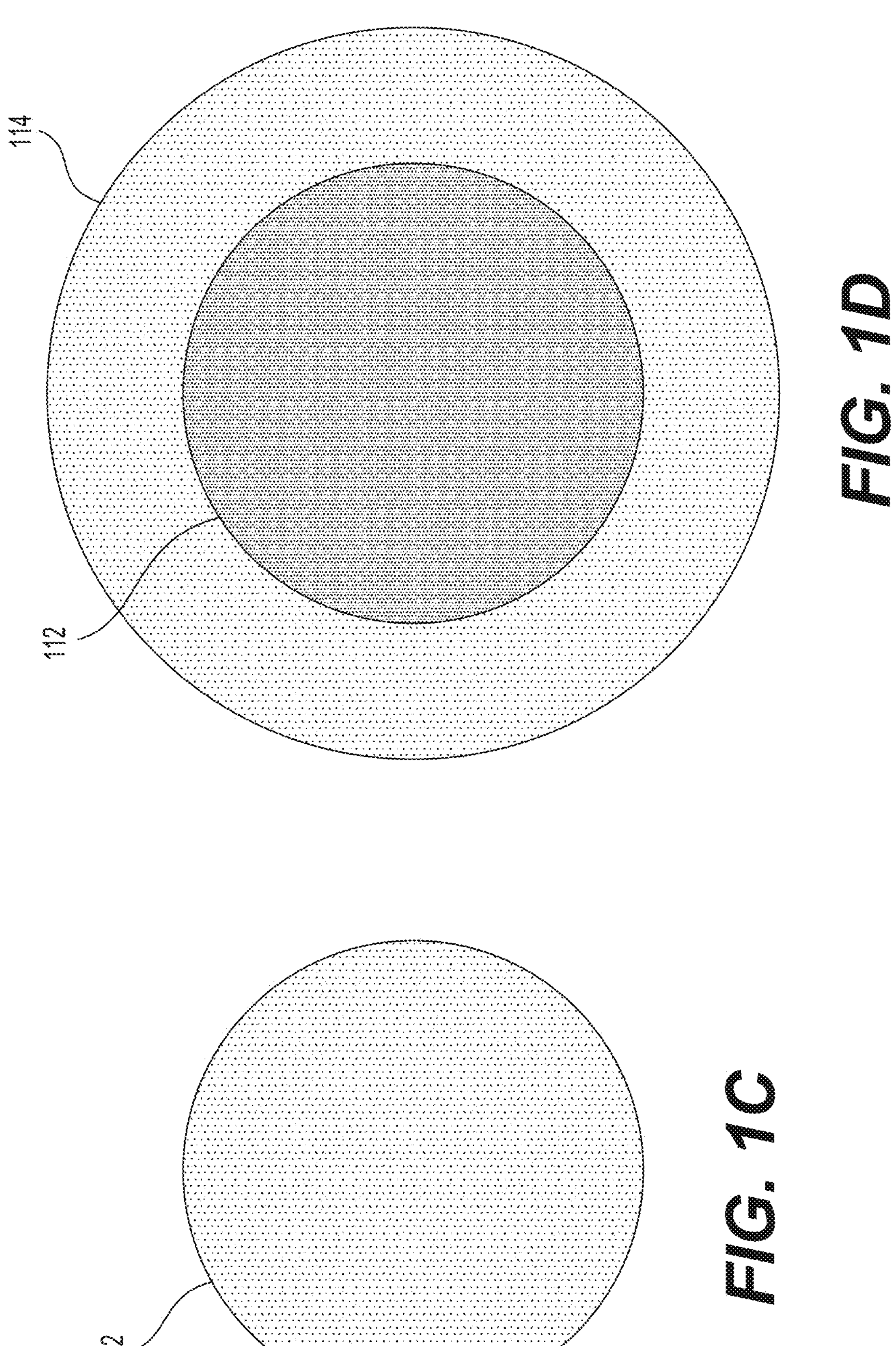
FIGS. 1C and 1D each illustrate extents to which the full eye pupil serves as an extrinsic entrance pupil, according to different embodiments of the present disclosure.

FIGS. 1C and 1D each illustrate extents to which eye pupil serves as the system entrance pupil, according to different embodiments of the present disclosure. FIG. 1C illustrates that, in the event that the camera housing 102 does not include an aperture stop which forms an intrinsic entrance pupil, an extrinsic entrance pupil is defined by a pupil 112 of a patient. FIG. 1D illustrates that, in the event that the camera housing 102 includes an aperture stop which forms an intrinsic entrance pupil 114, it provides an area larger than the pupil 112, and with appropriate alignment, the intrinsic entrance pupil 114 may fully encompass or surround an extrinsic entrance pupil defined by a pupil 112 of a patient within its field of view.

In contrast, according to conventional fundus cameras, optical mechanisms define an entrance pupil which is smaller in diameter than the pupil of the patient, so that a photographer faces substantial dexterity challenge in manually aligning the even narrower entrance pupil of the camera with the already millimeter-scale opening provided by the pupil of the human eye. Regardless of whether FIG. 1C or FIG. 1D is referred to, according to example embodiments of the present disclosure, according to the systems and devices described herein, a photographer or user encounters substantially less dexterity challenge in manually aligning the camera, or aligning the wider intrinsic entrance pupil of the camera, with the opening provided by the pupil of the human eye.

The camera housing 102 includes one or more eye illumination apparatuses 110 configured to pass light into an eye of a patient through a non-pupillary path, while maintaining substantially low-light conditions within the eye enclosure 104 while the camera housing 102 is fastened to a head of a patient. By way of example, an eye illumination apparatus 110 within the eye enclosure 104 may include an outer cover enclosing a light source, the outer cover being opaque to light in substantially most directions except in one direction, such that, within the camera housing 102, the eye illumination apparatus 110 may cast light from the light source through a non-pupillary path into an eye of the patient while maintaining substantially low-light conditions within the eye enclosure 104. Such non-pupillary paths within the eye enclosure 104 can include any, some, or all of a trans-scleral path, a trans-palpebral path, and a trans-pars-planar path, or general any path which does not pass through the pupil or cornea.

By way of another example, an eye illumination apparatus outside the eye enclosure 104 (not illustrated herein) may, without regard as to the inclusion of an outer cover, include a light source which can cast light through a non-pupillary path into an eye of the patient from outside the eye enclosure 104. In this arrangement, additional light from the light source is substantially excluded by the eye enclosure 104, thereby maintaining substantially low-light conditions within the eye enclosure 104. Such non-pupillary paths outside the eye enclosure 104 can include a trans-temple path through skin and muscle of the forehead, through an orbit of the skull.

In conventional cameras, an aperture stop is positioned between a prime lens and the image sensor, where the aperture stop limits light which can pass through the aperture stop onto the image sensor and forms an entrance pupil. In contrast, in a camera according to example embodiments of the present disclosure, an aperture stop is not necessarily positioned between the prime lens and the image sensor in all examples.

Instead, according to some example embodiments of the present disclosure, due to the eye enclosure 104 substantially excluding outside light from the internal cavity of the camera housing 102, incident light emitted outward through a pupil of a patient is inherently narrowed before it is incident upon an entry optic and an image sensor. In this fashion, by configuration of the eye enclosure 104 and configuration of eye illumination apparatuses to maintain low-light conditions within the eye enclosure 104, incident light from a pupil of a patient is substantially the only light within the eye enclosure 104 detectable by an image sensor.

Moreover, due to the substantially low-light conditions within the eye enclosure 104, pupils of a patient tend to naturally dilate to adapt to the low-light conditions. Thus, the incident light will be naturally widened slightly, facilitating a camera capturing the incident of light as an image.

Alternatively, according to some example embodiments of the present disclosure, an aperture stop is included in the entry optic to form an intrinsic entrance pupil. Such examples are illustrated with reference to FIG. 2C, by way of example.

Additionally, since the non-pupillary path for light and the imaging path of the camera sensor do not substantially coincide, visual artifacts such as glares, haloes, reflections, and the like do not result from the operation of a fundus imaging device 100 according to example embodiments of the present disclosure, and cameras of the fundus imaging device 100 do not need to include polarizers in their imaging path to mitigate visual artifacts.

As a consequence of the exclusion of polarizers in the imaging path, to capture an image of the same brightness compared to conventional fundus cameras, cameras of the fundus imaging device 100 use substantially less incident light and therefore less illuminance on the retina, compared to illuminance required to operate a conventional fundus camera (by way of example, up to 90% less illuminance on the retina and up to 2.5 times more optical transmittance). The lowered illuminance on the retina significantly improves patient comfort during the photography process. The lowered illuminance may also increase a depth of field of a focus area in images captured by the cameras, thereby improving the likelihood that the images are in focus across the eye of the user.

Figures 2A, 2B:
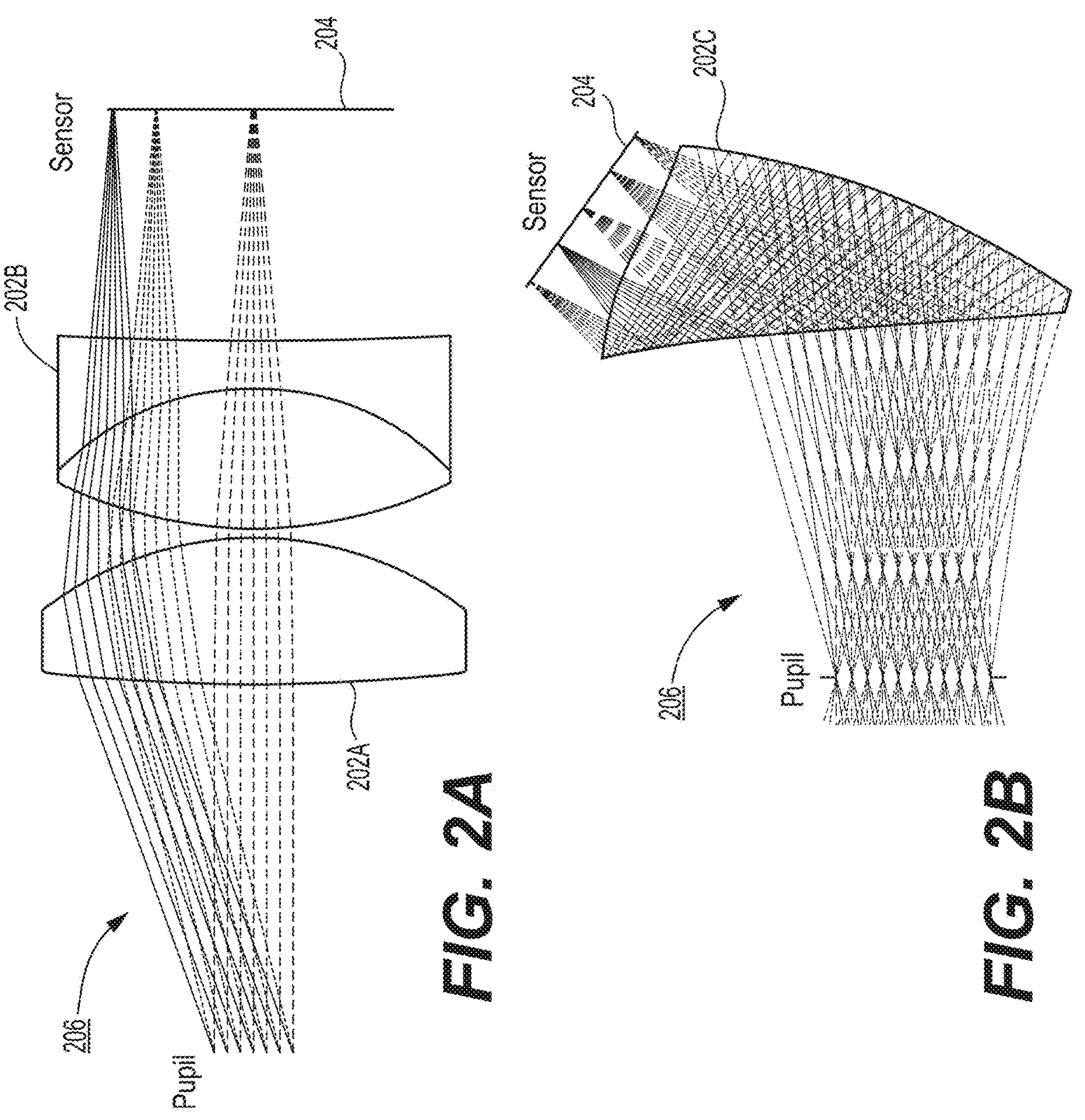
FIG. 2A illustrates an arrangement of an objective lens assembly and an image sensor according to example embodiments of the present disclosure.
FIG. 2B illustrates an arrangement of a mirror-backed prism and an image sensor according to example embodiments of the present disclosure.

By way of example, FIG. 2A illustrates an arrangement of an objective lens assembly including singlet lens 202A and doublet lens 202B, and an image sensor 204 according to example embodiments of the present disclosure, without an integral aperture stop. Incident light 206 from a pupil of a patient is incident upon the singlet lens 202A and doublet lens 202B. The incident light 206 is focused as it passes through the singlet lens 202A and doublet lens 202B, so that the incident light 206 forms an image on an image sensor 204.

By way of another example, FIG. 2B illustrates an arrangement of a mirror-backed prism 202C and an image sensor 204 according to example embodiments of the present disclosure, without an integral aperture stop. Incident light 206 from a pupil of a patient is incident upon the mirror-backed prism 202C. The incident light 206 is focused as it passes into the mirror-backed prism 202C, but does not pass through the mirror-backed prism 202C, and is rather reflected by the mirrored back of the prism 202C. The incident light 206 is internally reflected within the mirror-backed prism 202C, exiting in the direction of an image sensor 204 lateral to the mirror-backed prism 202C, and forms an image on the image sensor 204.

Thus, one or more cameras of a fundus imaging device 100 according to example embodiments of the present disclosure are configured to capture fundus images as described below. In some examples, each camera of the one or more cameras may include an entry optic and an image sensor without necessarily an integral aperture stop. In an illustrative example, the fundus imaging device 100 illuminates an eye of a patient by a non-pupillary path by the operation of one or more eye illumination apparatuses and a narrowed incident light emitted through a pupil of the user is focused by an entry optic to form an image on an image sensor. Where the camera does not include an integral aperture stop, the camera also does not form an intrinsic entrance pupil.

In such fashions, a camera according to example embodiments of the present disclosure can reduce optical components to an entry optic, to the exclusion of other optics. According to such example embodiments of the present disclosure, the reduction of optical components can further improve transmittance and thus lower the required illuminance on the retina as earlier described.

Figure 2C:
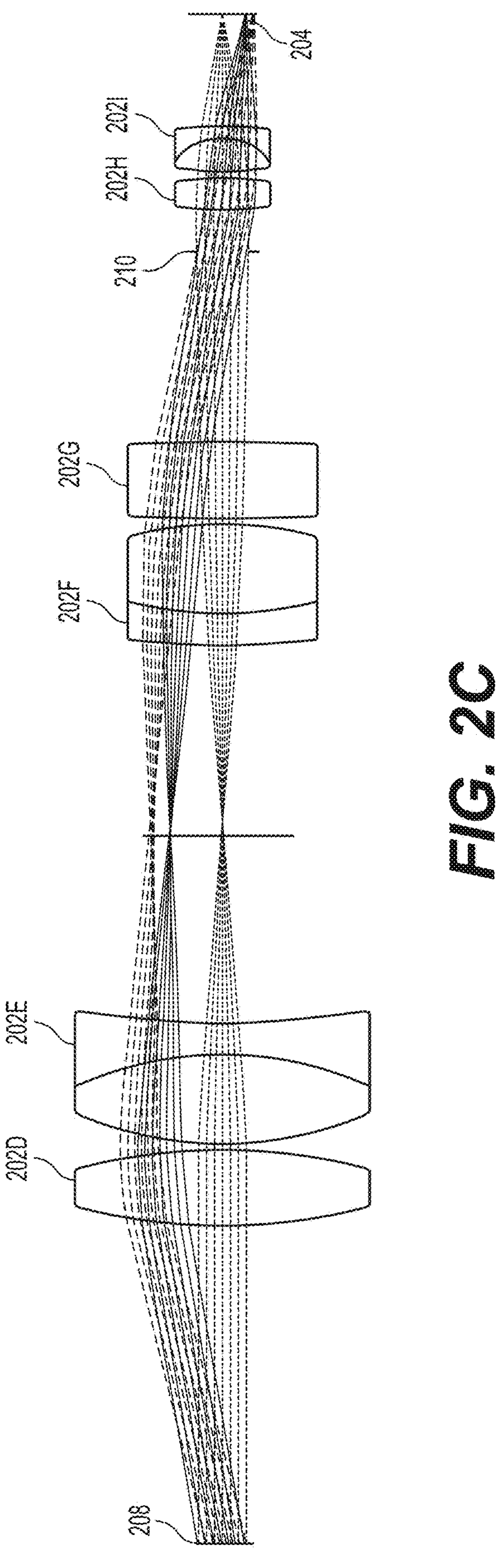
FIG. 2C illustrates an arrangement of optics between an intrinsic entrance pupil and an image sensor according to example embodiments of the present disclosure.

By way of another example, FIG. 2C illustrates an arrangement of objective lenses 202D and 202E, as well as relay lenses 202F, 202G, 202H, and 202I, between an intrinsic entrance pupil 208 and the image sensor 204. Along the light path, an integral aperture stop 210 defines the intrinsic entrance pupil 208. The arrangement of FIG. 2C can include any combination of optics and mirrors to establish light paths of various length to fit within the camera housing 102, such that the incident light is focused upon the image sensor 204.

An intrinsic entrance pupil 208, as described above, is wider in diameter than a pupil of a patient, while being in accordance with a diameter of the integral aperture stop 210. In this fashion, the arrangement of FIG. 2C facilitates manually aligning a field of view provided by the wider intrinsic entrance pupil of the camera with the opening provided by the pupil of the human eye, as described above with reference to FIG. 1D.

An entry optic of a fundus imaging device 100 may include a lens, a prism, a Fresnel lens, a mirror, a lenslet array or a metalens. It may, but need not, include zoom lens having mechanical assemblies allowing variation of focal length. Since each camera of a fundus imaging device 100 is configured to perform fundus photography at a small range of possible focal lengths, they do not need to mechanically zoom to substantially variable focal lengths. Rather, the fundus imaging device 100 can be configured by computer-executable instructions stored on one or more memories to perform digital zoom, by one or more processors, on captured images to simulate a small range of possible focal lengths. In some examples, the imaging device 100 may be equipped with a liquid lens or other lens that may have focus changed based on a signal from one or more processors.

Alternatively, the fundus imaging device 100 may further include a zoom lens allowing variation of focal length.

An entry optic which is a lens can be a high-magnification lens, which may have a diopter value of 20 diopters or more. By way of example, aspheric lenses found in fundus cameras can have a diopter value of 40 diopters, 60 diopters, 90 diopters, and the like; and any of these aspheric lenses may be included in one or more cameras of a fundus imaging device 100 as an entry optic, providing high visual magnification of a patient's fundus.

An image sensor can be a sensor having higher sensitivity than conventional camera sensors, configured to capture images under low-light conditions. By way of example, an image sensor can be a high-sensitivity large-pixel (i.e., micrometer-scale pixel sensors) CMOS sensor or electron bombarded active pixel sensor. By way of another example, an image sensor can be a short-wavelength infrared ("SWIR") sensor instead of a CMOS sensor. By way of another example, an image sensor can be an image intensifier tube.

The fundus imaging device 100 can include multiple cameras, including at least a left camera and a right camera, each including a respective entry optic and a respective image sensor. A left camera can be configured to be positioned and oriented to capture incident light emitted from a pupil of a right eye of a patient. A right camera can be configured to be positioned and oriented to capture incident light emitted from a pupil of a left eye of a patient.

Furthermore, each camera of the one or more cameras, including its respective entry optic and image sensor may be configured by one or more mechanical actuators to swivel on one or more axes within a limited degree of freedom on each axis. Because patient eyes can freely move within the eye enclosure 104, a mechanical actuator can have degrees of freedom on each axis for each camera configured to orient the image sensor to capture a pupil of a respective eye within a range of possible orientations of the pupil. Therefore, a camera and mechanical actuators of the camera can be configured by computer-executable instructions stored on one or more memories to perform eye-tracking actuation, where one or more processors can be configured by computer-executable instructions stored on one or more memories to analyze an image of an eye of a patient captured by a camera; determine whether a pupil of a patient is substantially captured within the field of view; and signal one or more mechanical actuators of the camera to orient the camera to substantially capture the pupil of a patient in the field of view.

Alternatively, the fundus imaging device 100 can include only one camera, including an entry optic and an image sensor. A singular camera can be configured to be positioned and oriented such that it is laterally movable through the camera housing 102 by one or more mechanical actuators, into at least a first position where a left eye of a patient is substantially captured in the field of view of the camera, and a second position where a right eye of a patient is substantially captured in the field of view of the camera. The singular camera can be configured by computer-executable instructions stored on one or more memories to capture images of a left eye and a right eye in turn, in any order, alternating any number of times therebetween.

Because the camera housing 102 is fastened to a head of a patient, one or more cameras according to example embodiments of the present disclosure move along with the head of the patient, and maintain their position and orientation relative to the eyes of the patient. Thus, a clinician operating the fundus imaging device 100 does not need to manually align a camera field of view with a pupil of an eye of the patient, alleviating much physical dexterity and challenge in performing fundus photography.

According to example embodiments of the present disclosure, each camera of the one or more cameras can have a separate region of coverage, and each region of coverage is substantially non-overlapping with each other region of coverage of other cameras.

Furthermore, each camera of the one or more cameras can be configured by computer-executable instructions stored on one or more memories to capture still images, videos, and combinations thereof. One or more processors can receive input from an operator of the fundus imaging device 100 from an input device of the fundus imaging device 100 or from a remote input device in communication with the fundus imaging device 100, and capture still images, videos, or combinations thereof from one or more image sensors in accordance with the input. One or more processors can furthermore be configured by computer-executable instructions stored on one or more memories to capture still images, videos, or combinations thereof from only one camera at a time or from multiple cameras concurrently, and can be configured to capture still images, videos, and combinations thereof in accordance with schedules which are preconfigured or which are configured by input from an operator of the fundus imaging device 100 as described above.

Computer systems operated by clinicians can be configured to analyze videos captured by a fundus imaging device 100 according to example embodiments of the present disclosure to monitor observations over time, such as observations of patient blood flows, patient vital signs, patient white blood cell count, and the like. Moreover, computer systems operated by clinicians can be configured to analyze videos captured by a fundus imaging device 100 according to example embodiments of the present disclosure to capture highly magnified images for medical imaging. By way of example, in the course of performing diagnostic procedures on a patient such as fundus fluorescein angiography ("FFA") or indocyanine green angiography ("ICGA"), which can take place at regular magnification, vascular florescence introduced by dyes in a patient's bloodstream can be seen at high magnification in fundus imaging.

Furthermore, the fundus imaging device 100 can be configured to communicate with one or more devices over short-range communication, such as according to Bluetooth or other wireless protocols, or long-range networked communication, such as according to IEEE 802.11 or other wireless network protocols. One or more processors can furthermore be configured by computer-executable instructions stored on one or more memories to transmit still images, videos, or combinations thereof captured by the one or more cameras to other devices or computing systems configured to store, display, and analyze the captured still images, videos, or combinations thereof (collectively "captured images," for brevity).

Furthermore, the fundus imaging device 100 can be configured to display captured images on one or more internal or external display devices. By way of example, a fundus imaging device 100 can transmit captured images by an internal data bus to an internal display screen set in any side other than an eye-facing side. Alternatively, a fundus imaging device 100 can transmit captured images to an external device having a display screen by any short-range communication or long-range networked communication as described above. The internal display screen can be configured by computer-executable instructions stored on one or more memories to display or stream captured images over time. An external device having a display screen can also be configured by computer-executable instructions stored on one or more memories to display or stream captured images over time. In the event that the fundus imaging device 100 includes more than one camera, an internal display screen or an external device having a display screen can display or stream captured images from each camera concurrently.

In this fashion, the fundus imaging device 100 can provide a clinician operating the fundus imaging device 100 with a real-time image feed or video feed for review, to provide additional options for medical imaging.

Figure 3:
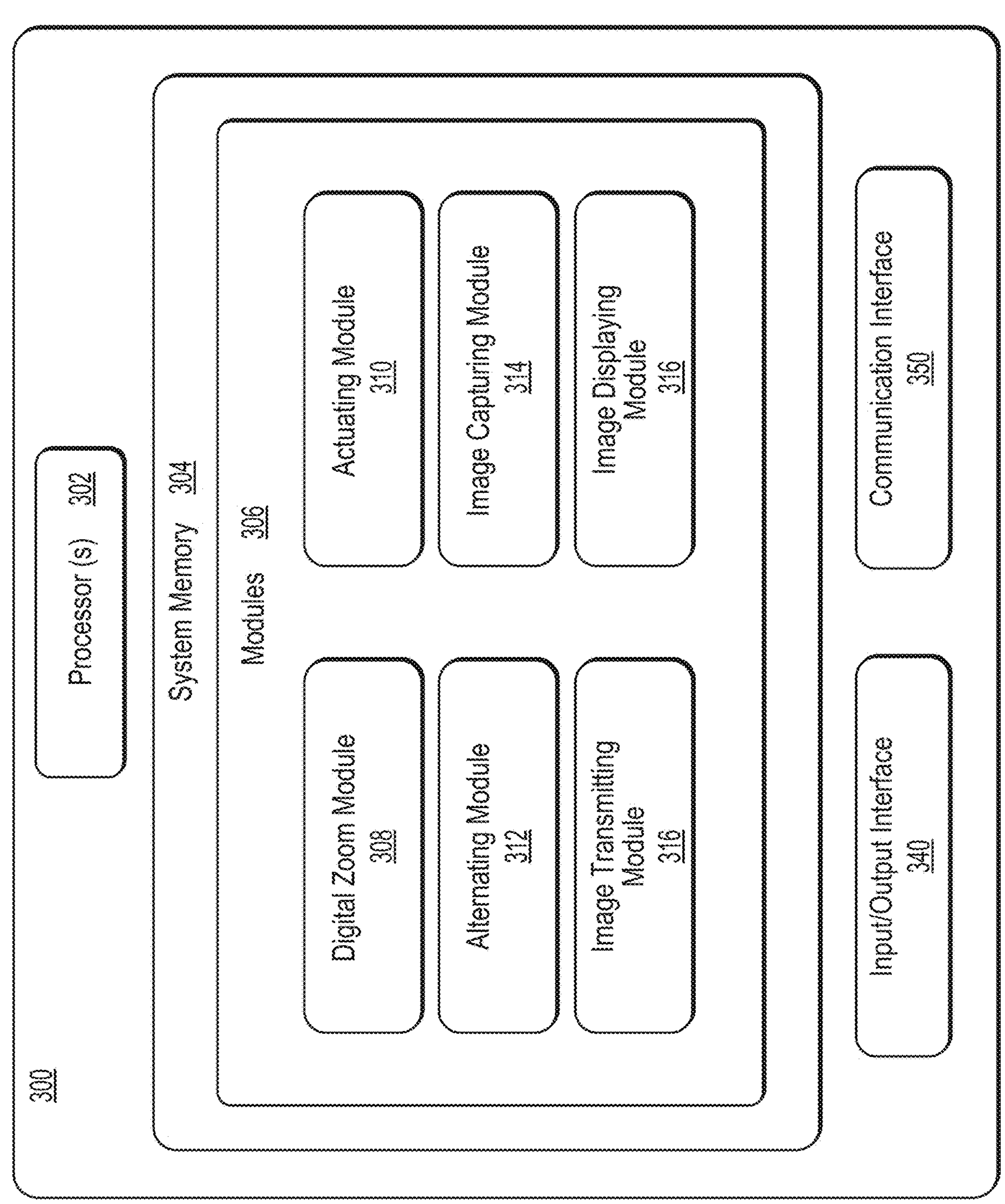
FIG. 3 illustrates an example system for implementing the processes and methods described herein for controlling a fundus imaging device.

FIG. 3 illustrates an example system 300 for implementing the processes and methods described above for controlling a fundus imaging device.

The techniques and mechanisms described herein may be implemented by multiple instances of the system 300 as well as by any other computing device, system, and/or environment. The system 300 shown in FIG. 3 is only one example of a system and is not intended to suggest any limitation as to the scope of use or functionality of any computing device utilized to perform the processes and/or procedures described above. Other well-known computing devices, systems, environments and/or configurations that may be suitable for use with the embodiments include, but are not limited to, personal computers, server computers, hand-held or laptop devices, multiprocessor systems, microprocessor-based systems, set top boxes, game consoles, programmable consumer electronics, network PCs, minicomputers, mainframe computers, distributed computing environments that include any of the above systems or devices, implementations using field programmable gate arrays ("FPGAs") and application specific integrated circuits ("ASICs"), and/or the like.

The system 300 may include one or more processors 302 and system memory 304 communicatively coupled to the processor(s) 302. The processor(s) 302 may execute one or more modules and/or processes to cause the processor(s) 302 to perform a variety of functions. In some embodiments, the processor(s) 302 may include a central processing unit ("CPU"), a graphics processing unit ("GPU"), both CPU and GPU, or other processing units or components known in the art. Additionally, each of the processor(s) 302 may possess its own local memory, which also may store program modules, program data, and/or one or more operating systems.

Depending on the exact configuration and type of the system 300, the system memory 304 may be volatile, such as RAM, non-volatile, such as ROM, flash memory, miniature hard drive, memory card, and the like, or some combination thereof. The system memory 304 may include one or more computer-executable modules 306 that are executable by the processor(s) 302.

The modules 306 may include, but are not limited to, a digital zoom module 308, an actuating module 310, an alternating module 312, an image capturing module 314, an image transmitting module 316, and an image displaying module 318.

The digital zoom module 308 can configure one or more processors 302 to perform digital zoom on captured images as described above.

The actuating module 310 can configure one or more processors 302 to analyze an image of an eye of a patient captured by a camera; determine whether a pupil of a patient is substantially captured within the field of view; and signal one or more actuators of the camera to re-orient the camera to substantially capture the pupil of a patient in the field of view as described above.

The alternating module 312 can configure one or more processors 302 to capture images of a left eye and a right eye in turn as described above.

The image capturing module 314 can configure one or more processors 302 to capture still images, videos, or combinations thereof from one or more image sensors as described above.

The image transmitting module 316 can configure one or more processors 302 to transmit still images, videos, or combinations thereof captured by the one or more cameras to devices or computing systems as described above.

The image displaying module 318 can configure one or more processors 302 to display or stream captured images over time as described above.

The system 300 may additionally include an input/output (I/O) interface 340 for receiving input from the image sensor, and for outputting captured images to a format displayable by an internal display device or by an external device having a display screen. The system 300 may also include a communication module 350 allowing the system 300 to communicate with such external devices over short-range communication or over a long-range network. The network may include the Internet, wired media such as a wired network or direct-wired connections, and wireless media such as acoustic, radio frequency ("RF"), infrared, and other wireless media.

Some or all operations of the methods described above can be performed by execution of computer-readable instructions stored on a computer-readable storage medium, as defined below. The term "computer-readable instructions" as used in the description and claims, include routines, applications, application modules, program modules, programs, components, data structures, algorithms, and the like. Computer-readable instructions can be implemented on various system configurations, including single-processor or multiprocessor systems, minicomputers, mainframe computers, personal computers, hand-held computing devices, microprocessor-based, programmable consumer electronics, combinations thereof, and the like.

The computer-readable storage media may include volatile memory (such as random-access memory ("RAM")) and/or non-volatile memory (such as read-only memory ("ROM"), flash memory, etc.). The computer-readable storage media may also include additional removable storage and/or non-removable storage including, but not limited to, flash memory, magnetic storage, optical storage, and/or tape storage that may provide non-volatile storage of computer-readable instructions, data structures, program modules, and the like.

A non-transient computer-readable storage medium is an example of computer-readable media. Computer-readable media includes at least two types of computer-readable media, namely computer-readable storage media and communications media. Computer-readable storage media includes volatile and non-volatile, removable and non-removable media implemented in any process or technology for storage of information such as computer-readable instructions, data structures, program modules, or other data. Computer-readable storage media includes, but is not limited to, phase change memory ("PRAM"), static random-access memory ("SRAM"), dynamic random-access memory ("DRAM"), other types of random-access memory ("RAM"), read-only memory ("ROM"), electrically erasable programmable read-only memory ("EEPROM"), flash memory or other memory technology, compact disk read-only memory ("CD-ROM"), digital versatile disks ("DVD") or other optical storage, magnetic cassettes, magnetic tape, magnetic disk storage or other magnetic storage devices, or any other non-transmission medium that can be used to store information for access by a computing device. In contrast, communication media may embody computer-readable instructions, data structures, program modules, or other data in a modulated data signal, such as a carrier wave, or other transmission mechanism. A computer-readable storage medium employed herein shall not be interpreted as a transitory signal itself, such as a radio wave or other free-propagating electromagnetic wave, electromagnetic waves propagating through a waveguide or other transmission medium (such as light pulses through a fiber optic cable), or electrical signals propagating through a wire.

The computer-readable instructions stored on one or more non-transitory computer-readable storage media that, when executed by one or more processors, may perform operations described above with reference to FIGS. 1-2B. Generally, computer-readable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the processes.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. An imaging device, comprising:
- a camera housing configured to fasten to a head of a patient;
- an eye enclosure configured to enclose an area around eyes of the patient;
- a camera positioned within an internal cavity of the camera housing and directed towards an eye of the patient; and
- an eye illumination apparatus disposed within the eye enclosure and comprising an outer cover enclosing a light source, the outer cover being opaque to light in substantially most directions except in one direction and is configured to pass light into an eye of a patient through a non-pupillary path, while maintaining a low-light condition within the eye enclosure while the camera housing is fastened to a head of a patient
- wherein the camera comprises an entry optic and an image sensor; and
- wherein the camera comprises an intrinsic entrance pupil having a diameter greater than 4 mm.

2. The imaging device of claim 1, wherein a light-sensitive side of the camera is positioned in the internal cavity toward an eye-facing side of the camera housing.

3. The imaging device of claim 1, wherein the non-pupillary path comprises a trans-temple path through a forehead of the patient.

4. The imaging device of claim 1, wherein the non-pupillary path and an imaging path of the image sensor do not coincide.

5. The imaging device of claim 1, wherein the entry optic of the camera comprises a mirror-backed prism, and the image sensor is disposed lateral to the mirror-backed prism.

6. The imaging device of claim 1, wherein the camera further comprises a mechanical actuator having degrees of freedom configured to orient the image sensor to capture a pupil of an eye of a patient within a range of possible orientations of the pupil.

7. The imaging device of claim 6, further comprising one or more processors configured by computer-executable instructions stored on one or more non-transitory computer-readable media to:
- analyze an image of the eye of the patient captured by the camera;
- determine, based at least in part on the image of the eye, whether the pupil of the patient is captured within a field of view of the camera; and
- signal the mechanical actuator to orient the camera to capture the pupil in the field of view.

8. The imaging device of claim 1, further comprising a second camera, wherein the second camera further comprises a second entry optic and a second image sensor;
- wherein the camera is configured to capture incident light emitted from a pupil of a right eye of a patient; and
- wherein the second camera is configured to capture incident light emitted from a pupil of a left eye of a patient.

9. The imaging device of claim 1, wherein the camera is laterally positionable within the camera housing by a mechanical actuator into at least a first position where a left eye of a patient is substantially captured in a field of view of the camera, and a second position where a right eye of the patient is substantially captured in the field of view of the camera.

10. The imaging device of claim 1, further comprising one or more processors configured by computer-executable instructions stored on one or more non-transitory computer-readable media to transmit an image captured by the camera to a device or computing system configured to store, display, and analyze the image.

11. An imaging device, comprising:
- a camera housing configured to fasten to a head of a patient;
- an eye enclosure configured to enclose an area around eyes of the patient;
- a camera positioned within an internal cavity of the camera housing and directed towards an eye of the patient; and
- an eye illumination apparatus disposed outside the eye enclosure and comprising an outer cover and a light source casting light which is substantially excluded by the eye enclosure, the outer cover being opaque to light in substantially most directions except in one direction configured to pass light into an eye of a patient through a non-pupillary path, while maintaining a low-light condition within the eye enclosure while the camera housing is fastened to a head of a patient
- wherein the camera comprises an entry optic and an image sensor; and
- wherein the camera comprises an intrinsic entrance pupil having a diameter greater than 4 mm.

12. The imaging device of claim 11, wherein the eye enclosure is opaque to light and non-rigid and is configured to maintain the low-light condition within the eye enclosure while the camera housing is fastened to the head of the patient.

13. The imaging device of claim 12, wherein a light-sensitive side of the camera is positioned in the internal cavity toward an eye-facing side of the camera housing.

14. The imaging device of claim 11, wherein the non-pupillary path comprises a trans-temple path through a forehead of the patient.

15. The imaging device of claim 11, wherein the non-pupillary path and an imaging path of the image sensor do not coincide.

16. The imaging device of claim 11, wherein the entry optic of the camera comprises a mirror-backed prism, and the image sensor is disposed lateral to the mirror-backed prism.

17. The imaging device of claim 11, wherein the camera further comprises a mechanical actuator having degrees of freedom configured to orient the image sensor to capture a pupil of an eye of a patient within a range of possible orientations of the pupil.

18. The imaging device of claim 17, further comprising one or more processors configured by computer-executable instructions stored on one or more non-transitory computer-readable media to:
- analyze an image of the eye of the patient captured by the camera;
- determine, based at least in part on the image of the eye, whether the pupil of the patient is captured within a field of view of the camera; and
- signal the mechanical actuator to orient the camera to capture the pupil in the field of view.

19. The imaging device of claim 11, further comprising a second camera, wherein the second camera further comprises a second entry optic and a second image sensor;

wherein the camera is configured to capture incident light emitted from a pupil of a right eye of a patient; and wherein the second camera is configured to capture incident light emitted from a pupil of a left eye of a patient.

* * * * *